United States Patent [19]
Labat et al.

[11] Patent Number: 6,077,961
[45] Date of Patent: Jun. 20, 2000

[54] PURIFICATION OF THIOPENE

[75] Inventors: Yves Labat, Le Bouscat, France; Piet Luyendijk, Pays-Bas, Netherlands

[73] Assignee: Elf Atochem S.A., France

[21] Appl. No.: 09/251,408

[22] Filed: Feb. 17, 1999

[30]     Foreign Application Priority Data

Feb. 18, 1998  [FR]  France ................................. 98 01972

[51] Int. Cl.⁷ ................................................. C07D 333/08
[52] U.S. Cl. ............................................................ 549/83
[58] Field of Search ................................................. 549/83

[56]              References Cited
              U.S. PATENT DOCUMENTS

| | | |
|---|---|---|
| 3,197,483 | 7/1965 | Buchholz et al. . |
| 3,939,179 | 2/1976 | Bell et al. . |
| 5,166,362 | 11/1992 | Forquy et al. ............................. 549/83 |
| 5,723,039 | 3/1998 | Zosimov et al. ........................ 205/696 |
| 5,726,326 | 3/1998 | Hutchings et al. ....................... 549/85 |
| 5,767,229 | 6/1998 | Arretz et al. . |

FOREIGN PATENT DOCUMENTS

| | | |
|---|---|---|
| 2 742 144 | 6/1997 | France . |
| 2 742 145 | 6/1997 | France . |
| 2 742 157 | 6/1997 | France . |
| WO 97 21673 | 6/1997 | WIPO . |

OTHER PUBLICATIONS

Shemyakin et al, "Removal of sulfur compounds from natural gas", CA83:196007, 1975.

Labat et al, "Oxidative process for the purification of thiophene contaminated with mercaptans", CA131:157704, 1999.

French Search Report dated Nov. 2, 1998.

*Primary Examiner*—Deborah C. Lambkin

[57]              ABSTRACT

Process for purifying a thiophene contaminated by mercaptans comprising selectively oxidizing the mercaptans to form polysulphides, then distilling the thiophene in this way.

10 Claims, No Drawings

PURIFICATION OF THIOPENE

FIELD OF THE INVENTION

The present invention concerns the field of thiophene, and relates more particularly to the purification thereof.

BACKGROUND OF THE INVENTION

The synthesis of thiophene from $C_4$ raw materials such as furan, crotonaldehyde, butanol or butane, and sulphur compounds such as carbon disulphide, hydrogen sulphide and sulphur, may be accompanied by the formation of $C_4$ mercaptans (primary or secondary butyl mercaptan) which it is difficult to separate by distillation because their boiling points are close to that of thiophene. Furthermore, the presence of small quantities of mercaptans may modify the olfactory properties of commercial thiophene, and is therefore undesirable.

It is known to purify hydrocarbons containing sulphur impurities by adsorption on sieves, resins and adsorbents of various types. It is also known to oxidize the mercaptans contained in the hydrocarbons using air or oxygen. Unfortunately, these techniques cannot be employed for thiophene since it can itself be oxidized to form sulphoxides and/or sulphones.

Other techniques may also be used, for example solvent extraction, in particular using an aqueous sodium hydroxide solution. However, further to its poor efficiency and the need to use a large excess of sodium hydroxide which cannot be recycled, use of this method would lead to the formation of polluted aqueous effluents.

DESCRIPTION OF THE INVENTION

It has now been found that the oxidation of the mercaptans contained in thiophene by sulphur in the presence of a basic catalyst is fast and virtually complete, and makes it possible to form heavy polysulphides that can be separated with ease by distilling the thiophene.

The invention therefore relates to a process for purifying a thiophene contaminated by mercaptans, characterized in that it consists in selectively oxidizing the mercaptans to form polysulphides, then in distilling the thiophene treated in this way.

Oxidation of the mercaptans by sulphur requires the use of a basic catalyst. The use of an aqueous sodium hydroxide solution without the addition of sulphur may also be envisaged, but leads to the formation of aqueous effluents.

Basic catalysts making it possible to oxidize the mercaptans by sulphur are well known, and can all be used for implementation of the process according to the invention. Liquid basic catalysts can be used, but they have the drawback of being difficult to recycle in a new operation.

This is why, according to a preferred aspect of the invention, the basic catalyst is advantageously chosen from solid catalysts because, at the end of the reaction, they are easy to separate by filtration and can therefore be reused for another purification operation. When a solid catalyst is used, the first step in the process according to the invention can also be carried out continuously by forced circulation of the reactants (sulphur and the thiophene to be purified) through a column filled with solid catalyst; it is not even necessary to filter this catalyst at the end of the reaction.

EXAMPLES

The following may be mentioned as non-limiting examples of basic catalysts that can be used for oxidizing mercaptans to form polysulphides by reaction with sulphur:

aluminas, titanates, silicas or mixtures of these compounds, optionally modified by alkalis or alkaline-earth bases;

zeolites or hydrotalcites;

metal oxides or salts such as $Na_2O$, $K_1O$, $NaHCO_3$, $ZnO$, $MgO$, $ZrO_2$ and $CaCO_3$, it being possible for these compounds to be used as they are or, for some of them, fixed on a support (for example an alumina);

mercaptides or alcoholates such as RSNa, $RS(CH_2CH_2O)_nNa$ and $RO(CH_2CH_2O)_nNa$, R representing a $C_1$ to $C_{12}$ hydrocarbyl radical and n representing an integer ranging from 1 to 10;

amines, ammonium hydroxides, alkanolamines or metal hydroxides such as LiOH, NaOH and KOH.

According to another preferred aspect of the invention, the solid catalyst used is a basic anion-exchange resin such as, for example, a resin based on a styrene-divinylbenzene copolymer functionalized by primary, secondary or tertiary amino groups or by guanidine or amidine groups. These well-known basic resins are available on the market (for example, those with a tertiary amine functional group marketed by Rohm and Haas under the brand name Amberlyst®) or are described in the literature (Patents FR 2 742 144, FR 2 742 145 and FR 2 742 157).

The oxidation treatment according to the invention is carried out by dissolving, in the thiophene to be treated, a quantity of sulphur which may range from 1 to 10 gram-atoms of sulphur per mole of mercaptan present, preferably from 2 to 4.

The oxidation reaction may be carried out at a temperature ranging from room temperature to 120° C., but the procedure is preferably carried out at a temperature of between 60 and 90° C., which makes it possible to keep the thiophene in the liquid state and, at the same time, to dispose of the hydrogen sulphide produced by the reaction of oxidizing the mercaptans by sulphur. Above 90° C., it is necessary to operate under pressure, but this pressure should not be too high so as to make it possible to dispose of the hydrogen sulphide.

The amount of basic catalyst to be used can vary within wide limits. Relative to the weight of thiophene to be purified, it is generally between 0.1 and 10% in the case of a liquid catalyst, and between 0.5 and 15% in the case of a solid catalyst.

The procedure may be carried out in batch mode, with the reaction time depending on a variety of parameters such as the stirring, the amount of catalyst used and its chemical nature. In batch mode, from one to three hours of reaction are generally enough to convert 95% of the mercaptans present in the thiophene; better conversion can be obtained by extending the reaction time.

The procedure may also be carried out continuously, by making a stream of the thiophene to be purified, in which the sulphur needed for the oxidation reaction has been dissolved beforehand, circulate in a column packed with a fixed bed of solid catalyst (for example a basic resin).

The final distillation for separating the thiophene from the polysulphides which are formed may be carried out conventionally.

The following example illustrates the invention without limiting it.

EXAMPLE 1

400 g of thiophene contaminated by 0.4% of butyl mercaptans (mixture of primary and secondary mercaptans), 40 g of previously dried Amberlyst® A21 resin and 1.2 g of sulphur, which corresponds to an S/mercaptan molar ratio of about 2, are introduced into a 1 liter stirred reactor which is thermostatted.

After one hour of stirring at 80° C., 90% of the mercaptans had been converted, and 95% had been converted after 2 hours.

The thiophene treated in this way contained no more than 130 ppm of mercaptans after 4 hours of stirring. The reaction mixture was cooled and filtered to separate the resin, which was used for new operations with comparable efficacy.

After the filtrate was distilled, a thiophene was obtained whose mercaptan content, determined by potentiometry, was less than 100 ppm and which had lost all characteristic mercaptan odour.

EXAMPLE 2

5000 kg of thiophene contaminated by 0.52% of butyl mercaptans and 80 kg of sulphur, added in liquid form, were placed in a 6900 liter reactor. This mixture, heated to about 85° C. (reflux temperature) was circulated on a fixed bed consisting of 400 liters of Amberlyst® A21 resin washed beforehand with acetone then thiophene.

After about 2.5 hours, the circulation was stopped and about 4000 kg of thiophene were distilled from the reactor. The thiophene purified in this way had a mercaptan content (determined by potentiometry) of 300 ppm.

A new 4000 kg batch of contaminated thiophene was added to the heavy distillation residues which remained in the reactor and still contained excess sulphur, and the procedure (circulation then distillation) was repeated.

The initial amount of sulphur was enough to treat 6 batches in succession (i.e. 25,000 kg of thiophene in total) without adding sulphur.

After the sixth operation, and using more powerful distillation, 700 kg of thiophene could still be recovered, and this was recycled into another purification operation; the heavy distillation residues containing polysulphides with high boiling point, sulphur and a little thiophene were disposed of.

After 6 runs with 6 batches (36 batches in total), no deactivation of the resin was observed.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims.

I claim:

1. Process for purifying a thiophene contaminated by mercaptans, comprising selectively oxidizing the mercaptans to form polysulphides, then distilling the thiophene treated in this way.

2. Process according to claim 1 wherein the conversion of the mercaptans into polysulphides is obtained by oxidizing the mercaptans with sulphur in the presence of a basic catalyst.

3. Process according to claim 2, wherein the basic catalyst is a resin having amine, guanidine or amidine functional groups.

4. Process according to claim 1, wherein the oxidation is carried out by using from 1 to 10 gram-atoms of sulphur per mole of mercaptans.

5. Process according to claim 1, wherein the oxidation is carried out at a temperature ranging from room temperature to 120° C.

6. Process according to claim 2, wherein use is made of a liquid basic catalyst in a proportion of from 0.1 to 10% relative to the weight of thiophene to be purified.

7. Process according to claim 2, wherein use is made of a solid basic catalyst in a proportion of from 0.5 to 15% relative to the weight of thiophene to be purified.

8. Process according to claim 2, wherein the basic catalyst is a solid catalyst.

9. Process according to claim 4, wherein the oxidation is carried out using from 2 to 4 gram-atoms.

10. Process according to claim 5, wherein the temperature is between 60 and 90° C.

* * * * *